US011298487B2

(12) United States Patent
McMurray

(10) Patent No.: US 11,298,487 B2
(45) Date of Patent: Apr. 12, 2022

(54) ORAL MEDICAL APPARATUS

(71) Applicant: McMurray Medical Group, LLC, Minneapolis, MN (US)

(72) Inventor: Roxanne McMurray, Shoreview, MN (US)

(73) Assignee: McMurray Medical Group, LLC, Minneapolis, MN (US)

( * ) Notice: Subject to any disclaimer, the term of this patent is extended or adjusted under 35 U.S.C. 154(b) by 668 days.

(21) Appl. No.: 15/472,051

(22) Filed: Mar. 28, 2017

(65) Prior Publication Data
US 2017/0281888 A1 Oct. 5, 2017

Related U.S. Application Data

(60) Provisional application No. 62/314,678, filed on Mar. 29, 2016.

(51) Int. Cl.
*A61M 16/04* (2006.01)
*A61M 25/00* (2006.01)

(52) U.S. Cl.
CPC .... *A61M 16/0402* (2014.02); *A61M 16/0475* (2014.02); *A61M 25/0023* (2013.01); *A61M 16/0493* (2014.02); *A61M 16/0495* (2014.02); *A61M 2025/0025* (2013.01); *A61M 2205/0216* (2013.01)

(58) Field of Classification Search
CPC .......... A61M 16/0402; A61M 16/0475; A61M 16/0493; A61M 16/0495; A61M 2025/0025; A61M 2205/0216; A61M 25/0023; A61M 16/0427; A61M 16/0497
See application file for complete search history.

(56) References Cited

U.S. PATENT DOCUMENTS

| 4,166,467 | A | | 9/1979 | Abramson |
| 4,166,468 | A | * | 9/1979 | Haynie ............ A61M 16/0409 128/207.15 |
| 4,335,723 | A | | 6/1982 | Patel |
| 4,530,354 | A | | 7/1985 | Froilan |
| 4,640,273 | A | | 2/1987 | Greene et al. |
| 4,848,331 | A | | 7/1989 | Northway-Meyer |
| 4,919,126 | A | | 4/1990 | Baildon |

(Continued)

FOREIGN PATENT DOCUMENTS

WO WO-2016166498 A1 * 10/2016 ............ A61M 16/04

OTHER PUBLICATIONS

International Search Report in PCT/US17/24613 dated Jun. 21, 2017.

(Continued)

*Primary Examiner* — Valerie L Woodward
*Assistant Examiner* — Paige Kathleen Bugg
(74) *Attorney, Agent, or Firm* — Dicke, Billig & Czaja, PLLC

(57) ABSTRACT

An oral medical apparatus includes a flexible tube with a first portion adjacent a proximal end of the tube and a second portion adjacent to the first portion. A support is located within the upper portion to prevent compression or collapse of the upper portion of the tube. The oral medical apparatus can accommodate a rigid connector that may be directly coupled to an anesthesia breathing circuit or a medical breathing device.

23 Claims, 20 Drawing Sheets

(56) References Cited

U.S. PATENT DOCUMENTS

| | | | |
|---|---|---|---|
| 4,919,127 A * | 4/1990 | Pell | A61M 16/0463 |
| | | | 128/207.14 |
| 4,987,895 A | 1/1991 | Heimlich | |
| 4,990,143 A | 2/1991 | Sheridan | |
| 5,279,610 A * | 1/1994 | Park | A61M 16/0488 |
| | | | 606/108 |
| 5,590,643 A | 1/1997 | Flam | |
| 5,743,258 A | 4/1998 | Sato et al. | |
| 6,148,818 A | 11/2000 | Pagan | |
| 6,474,332 B2 | 11/2002 | Arndt | |
| 6,474,339 B1 | 11/2002 | Grosbois et al. | |
| 6,729,325 B2 | 5/2004 | Alfery | |
| 6,981,502 B2 | 1/2006 | McCormick et al. | |
| 7,171,962 B1 | 2/2007 | Bloem | |
| 7,870,860 B2 | 1/2011 | McCormick et al. | |
| 7,918,227 B1 | 4/2011 | Phythyon | |
| 8,220,461 B1 | 7/2012 | Guerra et al. | |
| 8,631,795 B1 * | 1/2014 | McMurray | A61M 16/04 |
| | | | 128/207.14 |
| 8,640,692 B2 | 2/2014 | Matioc | |
| 8,757,164 B2 | 6/2014 | Abramson | |
| D760,385 S | 6/2016 | McKee | |
| 2003/0217744 A1 | 11/2003 | Sugai et al. | |
| 2005/0183729 A1 | 8/2005 | Fischer, Jr. | |
| 2006/0174893 A1 * | 8/2006 | Kanowitz | A61F 5/055 |
| | | | 128/207.14 |
| 2007/0006884 A1 | 1/2007 | Abramson | |
| 2008/0142003 A1 | 6/2008 | Depel | |
| 2008/0230054 A1 * | 9/2008 | Prineas | A61B 1/267 |
| | | | 128/200.26 |
| 2009/0056721 A1 * | 3/2009 | Leboeuf | A61M 16/0493 |
| | | | 128/207.14 |
| 2009/0064998 A1 | 3/2009 | Bassili | |
| 2010/0154800 A1 * | 6/2010 | Chang | A61M 16/04 |
| | | | 128/207.15 |
| 2011/0180065 A1 | 7/2011 | Hajgato et al. | |
| 2011/0197895 A1 * | 8/2011 | Stephenson | A61M 16/0816 |
| | | | 128/207.14 |
| 2012/0048278 A1 * | 3/2012 | Yasick | A61M 16/0461 |
| | | | 128/207.14 |
| 2013/0025601 A1 * | 1/2013 | Waldron | A61M 16/0497 |
| | | | 128/207.14 |
| 2014/0034060 A1 | 2/2014 | Esnouf et al. | |
| 2014/0277066 A1 | 9/2014 | Schaeffer et al. | |
| 2015/0136123 A1 * | 5/2015 | Donlon | A61M 16/0497 |
| | | | 128/200.26 |
| 2015/0202396 A1 * | 7/2015 | Rohl | A61M 16/0409 |
| | | | 128/207.15 |
| 2015/0352304 A1 | 12/2015 | Leevan | |
| 2016/0051782 A1 | 2/2016 | Reed | |
| 2016/0129211 A1 * | 5/2016 | Bruggemann | A61M 16/0816 |
| | | | 128/207.14 |
| 2016/0235938 A1 * | 8/2016 | Khabiri | A61M 16/085 |
| 2017/0314719 A1 * | 11/2017 | Blake | A61M 39/00 |
| 2019/0076609 A1 * | 3/2019 | Donlon | A61M 16/0497 |

OTHER PUBLICATIONS

Universal Bite Block (Adult)—Bite Block Solutions for ET Tube Protection; BB Medical Technologies; http://bandb-medical.com/universal-bite-block-adult/, copyright 2010-2017; 2 pages.

Comparison of Ventilation with the Numask vs. Traditional Mask, A Prospective, Randomized, Crossover Study; Anesthesia & Analgesia; http://www.numask.com/review_article/24; copyright 2006-2011 NuMask, Inc.; 2 pages.

Workload Comparison of Intraoral Mask to Standard Mask Ventilation Using a Cadaver Model; Human Factors and Ergonomics Society; www.numask.com/review_article/27; copyright 2006-2011 NuMask, Inc.; 1 page.

Hopple, Joseph P. "Insert an Oropharyngeal Airway." EMS Airway, May 1, 2019, www.emsairway.com/2019/05/01/insert-oropharyngeal-airway/#gref.

Wood Library-Museum of Anesthesiology,"Guedel Oral Airways." Wood Library Museum of Anesthesiology, Feb. 1, 2021, www.woodlibrarymuseum.org/museum/guedel-oral-airways.

* cited by examiner

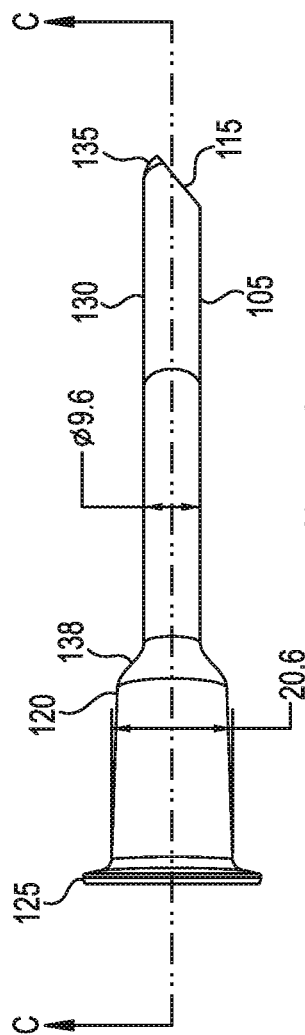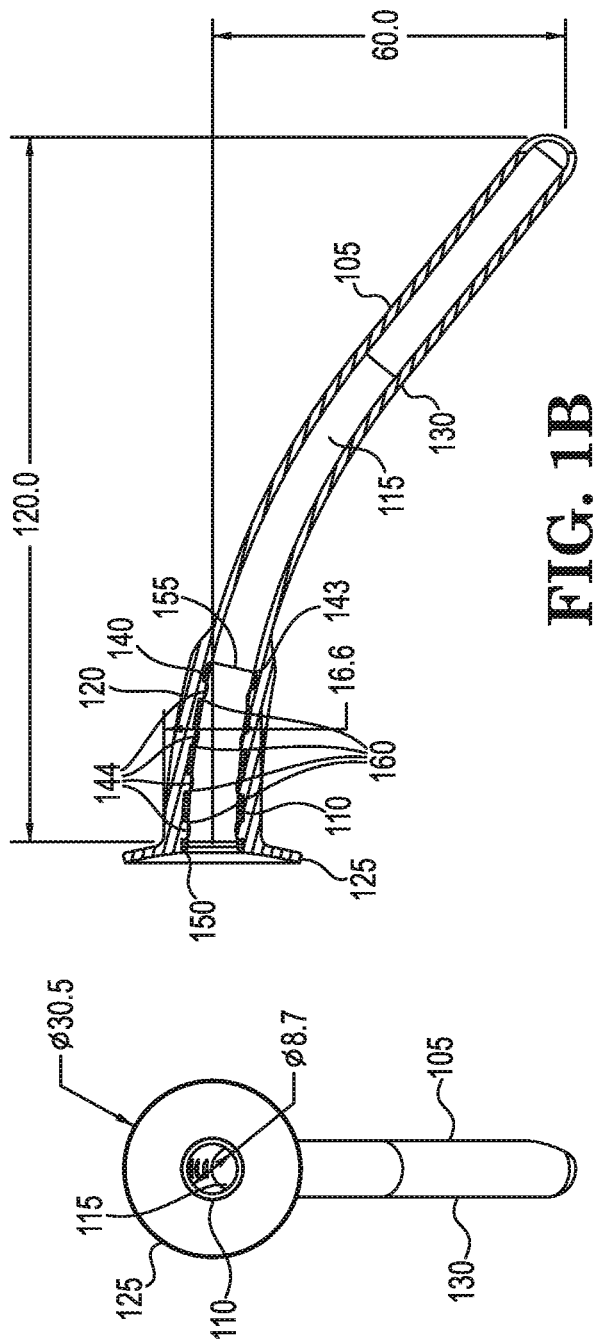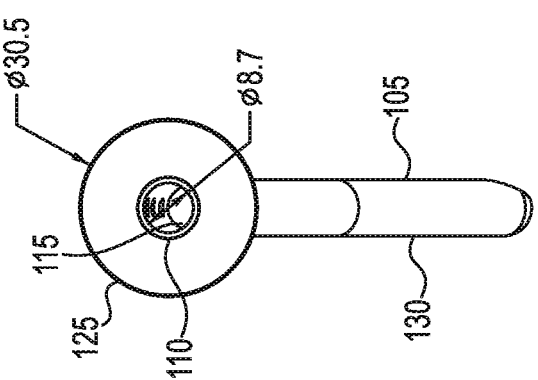

ORAL MEDICAL APPARATUS

CROSS REFERENCE TO RELATED APPLICATIONS

This application claims the benefit of U.S. Provisional Patent Application Ser. No. 62/314,678, filed Mar. 29, 2016, which is incorporated by reference herein.

FIELD OF THE DISCLOSURE

Embodiments of devices and related methods for improved oral medical apparatus are disclosed.

BACKGROUND

An oral or nasal medical apparatus relates to devices used to eliminate upper airway obstruction and facilitate oxygenation and ventilation in patients. These devices include the oropharyngeal airway, nasopharyngeal airway, endotracheal tube, laryngeal mask, and face-mask ventilation. An oropharyngeal airway (OPA), also referred to as an oral airway, is used to create an air passageway between the mouth and the posterior pharynx. Patients with sleep apnea, patients under anesthesia, or other patients with an obstructed airflow, may have an oral airway inserted to facilitate airflow.

Currently available oral airways include an outer surface made of a hard, rigid piece of plastic in a patient's mouth that is often poorly tolerated in conscious and semi-conscious patients. For instance, such rigid oral airways may induce gagging, vomiting, aspiration, layrngospasm, damage to teeth (due to patient biting), and damage to lips. If such an oral airway is left in place for a prolonged period of time, sores and swelling can develop in the mouth and tissue damage may occur. Improper sizing of these oral airways introduces problems as well. Given the rigid nature of oral airways, sizing must be done without error. A rigid oral airway that is too large can close the epiglottis and cut off an air supply. A rigid oral airway that is too small can cause tongue sores and swelling, and can also cause the airway to be obstructed by pharyngeal tissue if it fails to extend past the uvula.

Nasopharyngeal airways, also referred to as nasal airways, are also used to alleviate airway obstructions. They create an air passageway between the nose and posterior pharynx. Nasal airways may cause discomfort, increase heart rate and blood pressure, and can cause nasal injury and nosebleeds.

Endotracheal tubes (ETT) are inserted beyond the vocal cords into the trachea, which is farther into the oral passageway than an oral airway. ETTs are somewhat flexible and compressible, which enables a patient to collapse the ETT by biting, which can cut off the air supply and lead to hypoxia and/or negative pressure pulmonary edema. One advantage ETTs have over oral and nasopharyngeal airways is that they include an inflatable portion which creates a seal in the airway. This prevents oxygen diffusion into the surgical field.

Most laryngeal mask airway (LMA) are also flexible and compressible and are seated above the vocal cords. The patient can bite the LMA, collapse it, and cause an airway obstruction. The LMA also prevents oxygen diffusion into the surgical field.

Face-mask ventilation is commonly used to manually assist or control ventilation and breathing for the patient and to deliver oxygen, with or without an oral or nasopharyngeal airway. Delivery of oxygen via a mask can be compromised with an improper seal by facial hair, variations in facial structure, deficient dentition, and obesity. Inadequate ventilation and oxygenation can lead to hypoxia causing cell death, decrease in cognitive functioning, coma or death.

Patents under monitored anesthesia care (MAC) receiving supplemental oxygen via open delivery systems have an increased operating room fire risk. When patients require supplemental oxygen, as needed with heavy sedation for a procedure above the sternum, the electrocautery and oxygen become close in proximity, increasing the fire risk. Decreasing the oxygen concentration diffusion into the surgical field and supplying oxygen closer to the vocal cords, decreases the risk of a potential surgical fire and increases patient safety.

SUMMARY

In one embodiment, an airway apparatus includes a flexible tube having a proximal end, a distal end, a flange at the proximal end, an upper portion adjacent to the flange, a lower portion between the upper portion and the distal end, and a lumen that extends from the proximal end to the distal end. The flange has an outer diameter that is greater than an outer diameter of the upper portion. The upper portion has an outer diameter that is greater than that of the lower portion. The airway apparatus also includes a rigid support positioned within the upper portion of the tube that provides radial support of the upper portion and allows airflow from the proximal end to the distal end of the airway apparatus.

Other aspects of the invention will become apparent by consideration of the detailed description and accompanying drawings.

BRIEF DESCRIPTION OF THE DRAWINGS

FIG. 1A is a top side view of the airway apparatus of FIG. 1.

FIG. 1B is a longitudinal cross-sectional view of the airway apparatus of FIG. 1A taken along line C-C.

FIG. 1C is an end view of the airway apparatus of FIG. 1A.

DETAILED DESCRIPTION

Before any embodiments of the oral airway apparatus are described in detail, it is to be understood that the details of construction and the arrangement of components set forth in the following description or illustrated in the following drawings are exemplary and are not intended and should not be construed to limit the scope of the claims. The oral airway described herein is capable of other embodiments and of being practiced or of being carried out in various ways consistent with this specification. Various aspects or features of the oral airway apparatus disclosed herein may be used alone or in combination with other disclosed aspects or features.

Figure 12:
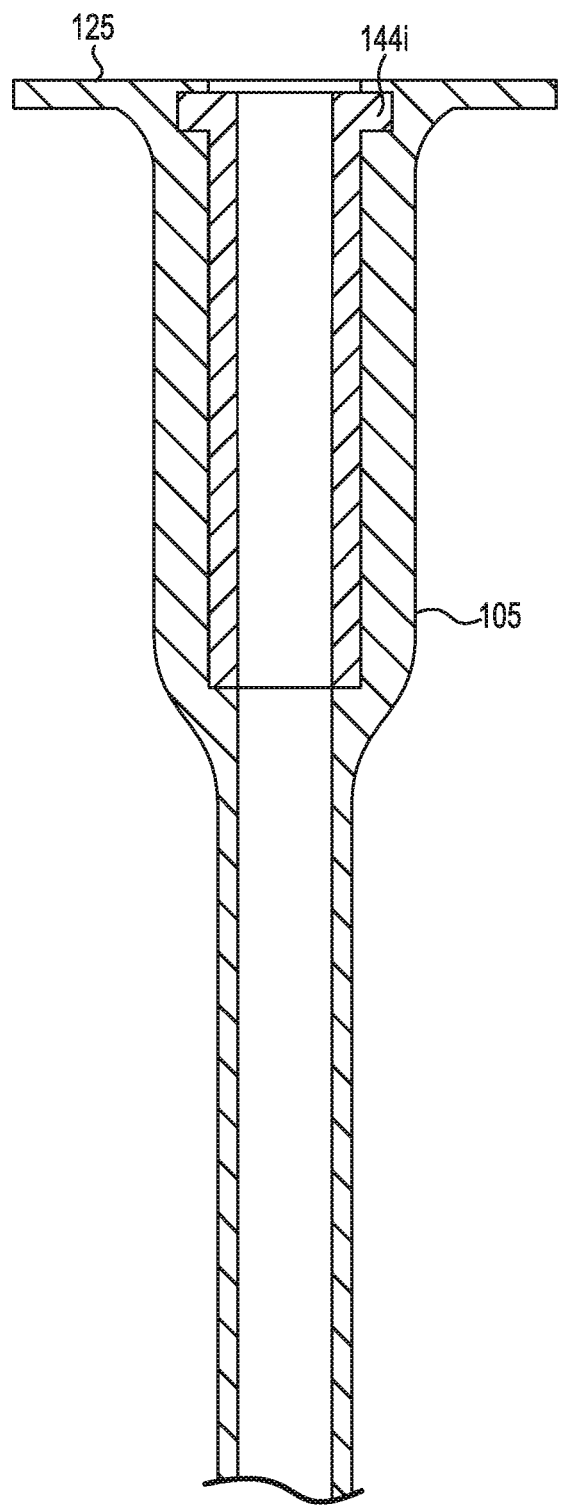
FIG. 12 is a diagrammatic longitudinal cross-sectional view of an alternative embodiment of a support structure for an airway apparatus.
Figure 13:
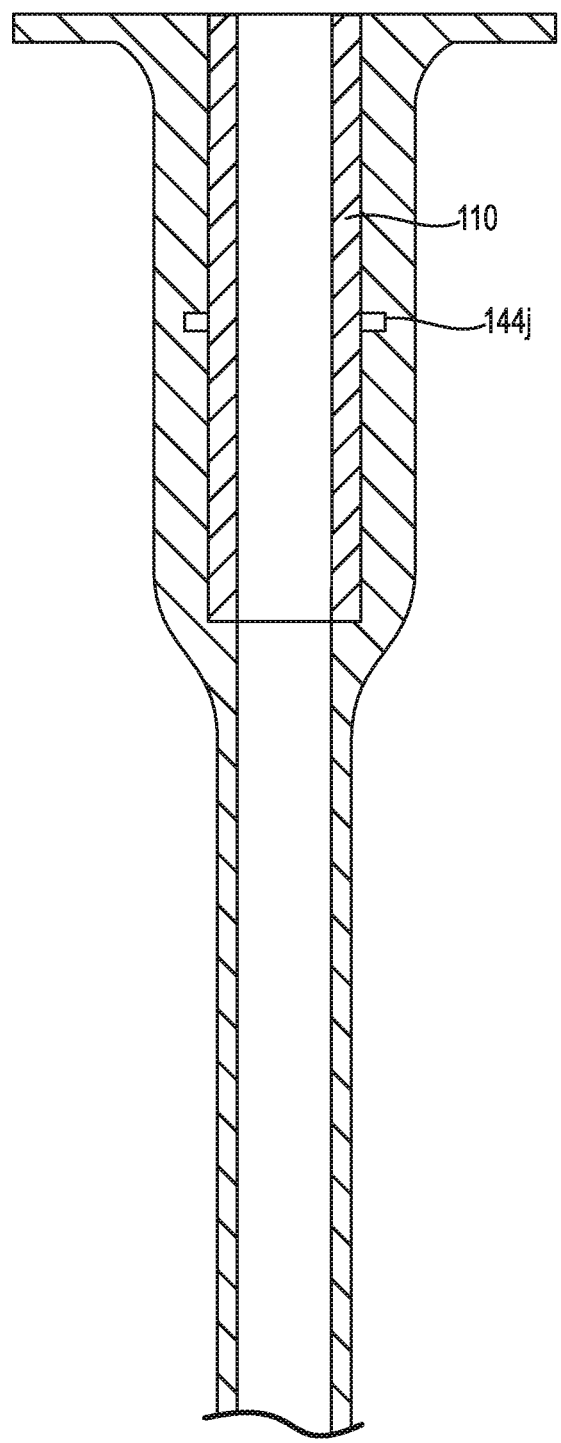
FIG. 13 is a diagrammatic longitudinal cross-sectional view of an alternative embodiment of a support structure for an airway apparatus.

FIGS. 1, 1A-C, 8, and 9 illustrate an airway apparatus 100 comprising a tube 105 and a support 110 positioned with an upper portion of tube 105, and a lumen 115. With reference to FIGS. 2-5, the illustrated tube 105 is a flexible and compressible tube made of, for instance, a latex free, soft thermoplastic elastomer, such as Mediprene® from Hexpot TPE, having a durometer of about shore A 50, or between about shore A 40-80. The illustrated tube 105 includes, a flange 125 at a proximal end of tube 105, an upper portion 120 adjacent to flange 125, and a lower portion 130 that extends from the upper portion 120 to a distal end 135. As illustrated, flange 125 is circular, although flange 125 may have other shapes such as oval, square, or rectangular. Lumen 115 extends from the proximal end to the distal end 115. In one embodiment, distal end 135 is blunt and may include a bevel. The outer surface of the upper portion 120 has an outer diameter less than an outer diameter of flange 125, and transitions at 138 to the lower portion 130, which has an outer diameter less than that of the upper portion. In the illustrated embodiment, flange 125 has an outer diameter of about 2.0 to about 3.0 centimeters, and the upper portion 120 has an outer diameter of about 1.6 to about 2.1 centimeters. In other embodiments, where flange 125 is not symmetrical about its axis, at least a portion of flange 125 has an outer diameter of about 2.0 to about 3.0 centimeters. In one embodiment, the transition portion 138 includes an outer diameter that gradually decreases from the upper portion 120 to the lower portion 130, providing a radially tapering profile in the view of FIG. 1. In the upper portion 120, lumen 115 defines a cavity 140 that has a greater inner diameter than the inner diameter of the lumen in the lower portion 130. In one embodiment, the inner surface of the tube includes a radial shoulder 143 defined by the transition of the inner diameter of the lumen 115 from the upper portion 120 to the lower portion 130. In one embodiment, a plurality of protrusions 144 are formed on the inner surface of the cavity 140. In the illustrated embodiment, the upper portion 120 includes eight protrusions 144a, 144b, 144c, 144d, 144e, 144f, 144g, 144h; however, in alternative embodiments, the upper portion 120 may include at least one or more protrusions 144. In one embodiment, the protrusion may be annular in shape. As shown in FIG. 12, in one embodiment, an annular protrusion 144i is located on the support 110 adjacent flange 125 at the proximal end of tube 105, and is over-molded by flange 125. As shown in FIG. 13, in one embodiment, an annular protrusion 144j is extends from the outer surface of support 110 at a location along the length of support 110. In alternative embodiments, the protrusions 144 are omitted (see, e.g., FIG. 10).

The tube 105 is designed in several sizes to accommodate the various pharynx sizes of patients. Below is an exemplary size chart for portions of the tube 105 based on estimated pharynx sizes by patient age. The size, length and diameter of the tube 105 are merely exemplary and should not be interpreted as limiting.

| Patient Age | Lower portion 130 Length (mm) | Lower portion 130 Inner Diameter (mm) | Lower portion 130 Outer Diameter (mm) | Upper portion 120 Length (mm) |
|---|---|---|---|---|
| 0-6 mo | 70 | 3.2 | 6.7 | 34 |
| 6 mo-1 yr | 80 | 3.9 | 7.4 | 35 |
| 1-4 yr | 90 | 4.5 | 8.0 | 36 |
| 5-8 yr | 100 | 5.2 | 8.7 | 36 |
| 8-10 yr | 110 | 5.9 | 9.4 | 38 |
| Adult female | 130 | 6.5 | 10 | 40 |
| Adult large male | 150 | 7.4 | 10.7 | 40 |

Figure 1:
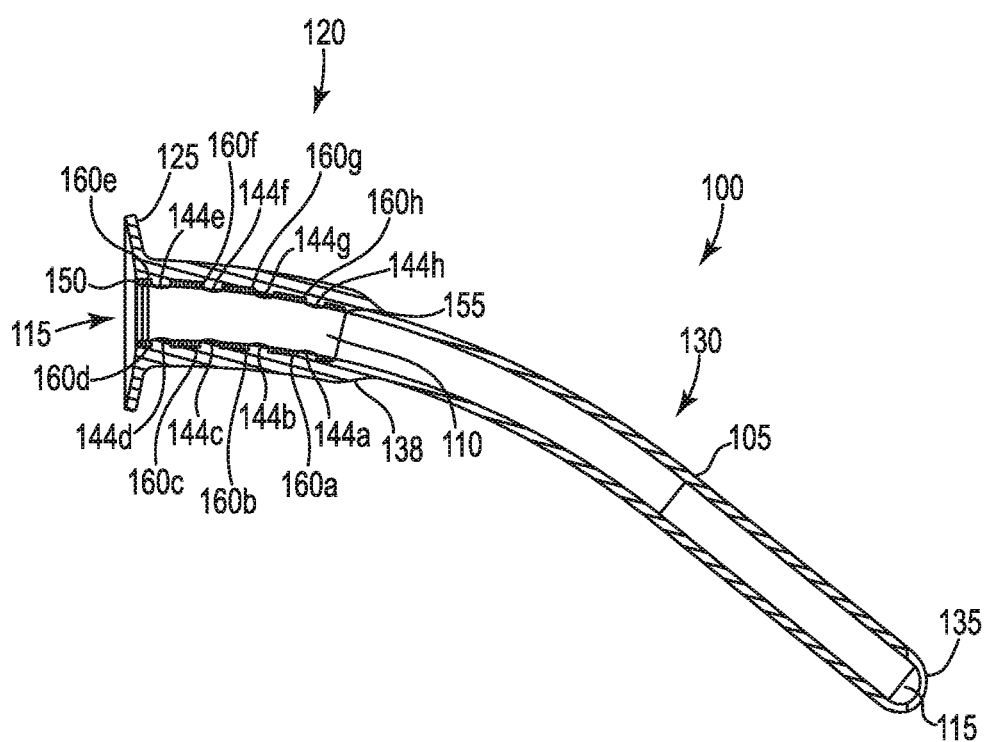
FIG. 1 is a partial longitudinal cross-sectional view of an airway apparatus according to one embodiment of the disclosure.
Figure 2:
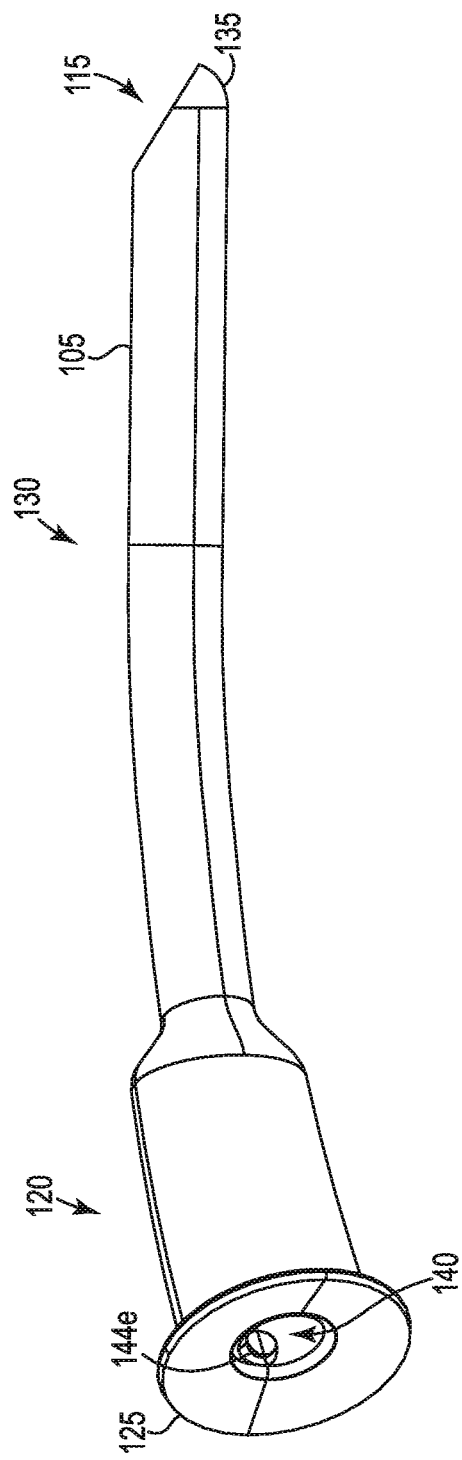
FIG. 2 is a first side view of the airway apparatus of FIG. 1.
Figure 3:
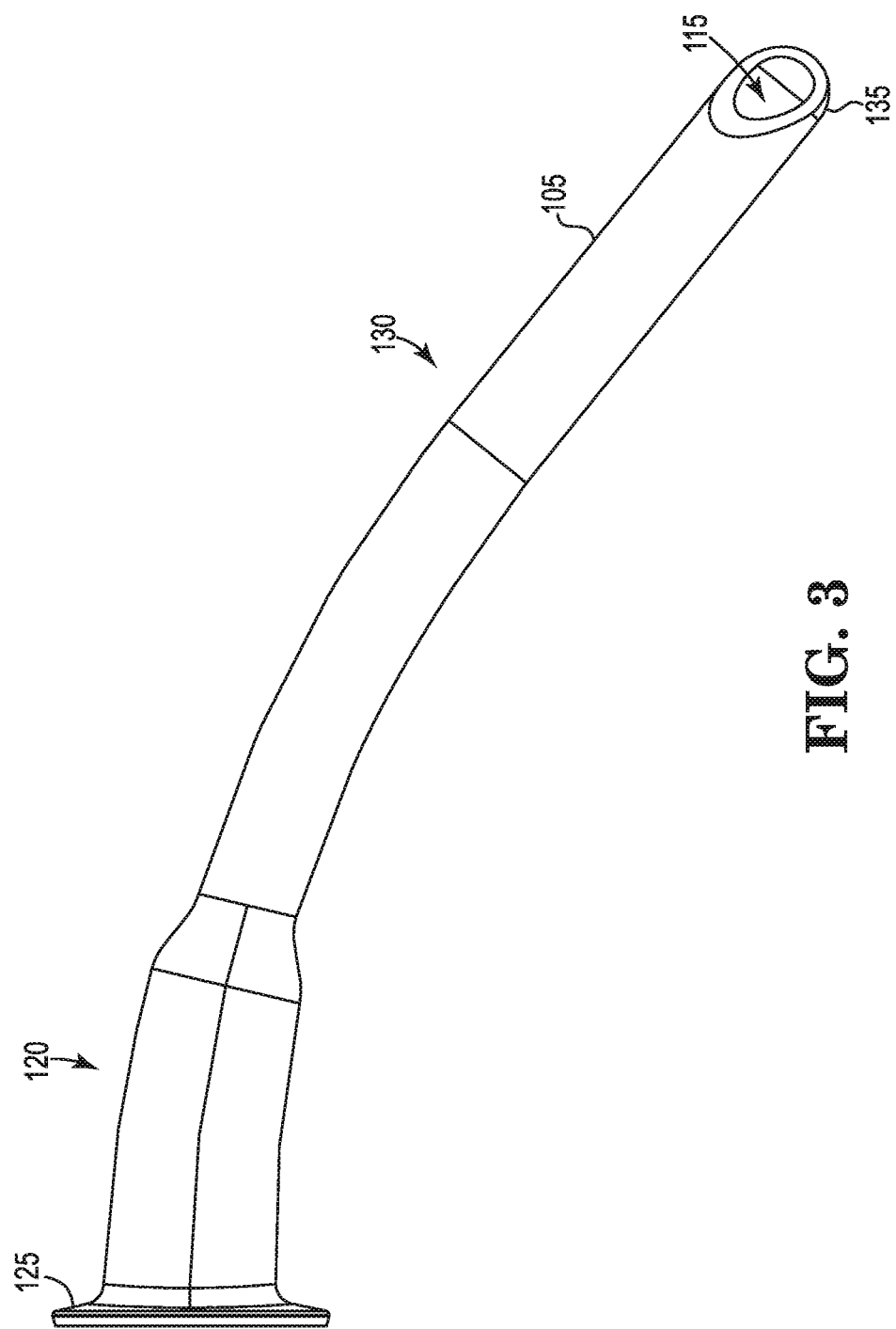
FIG. 3 is a second side view of airway apparatus tube of FIG. 1.
Figure 4:
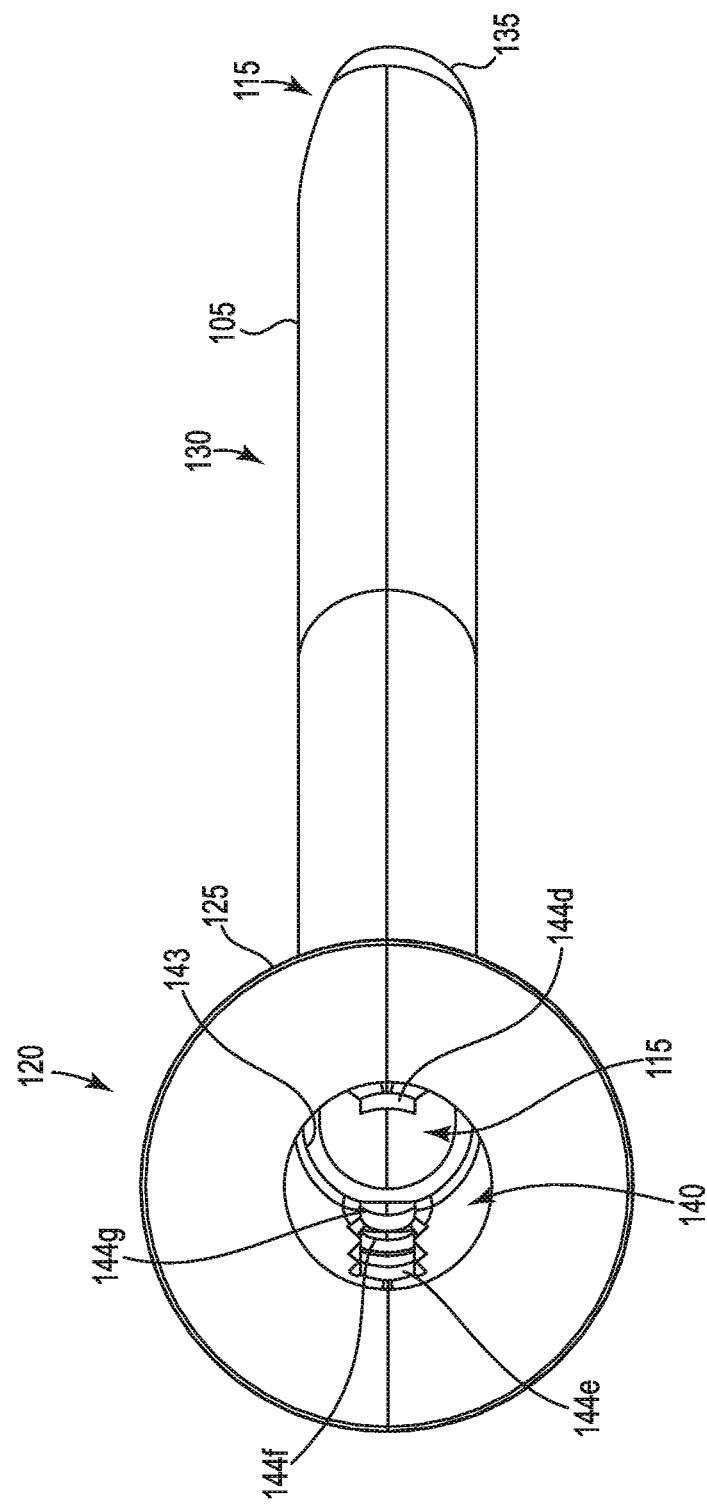
FIG. 4 is a front view of the airway apparatus of FIG. 1.
Figure 5:
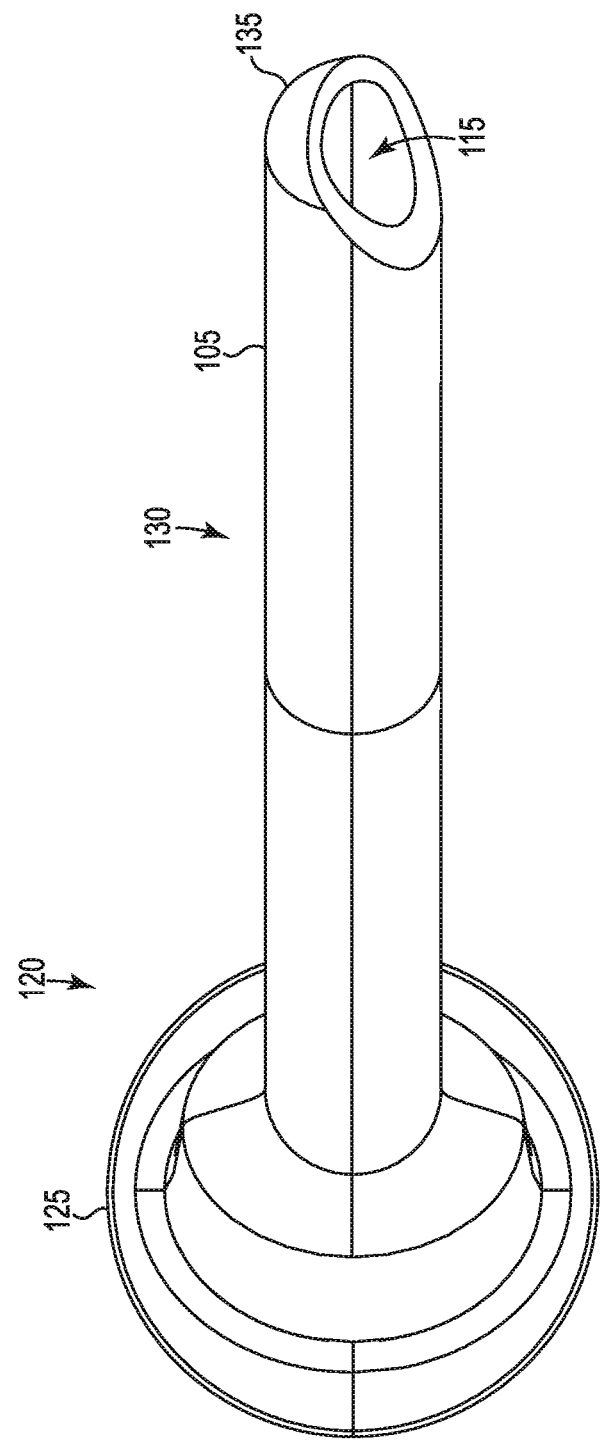
FIG. 5 is a rear view of the airway apparatus of FIG. 1.
Figure 6:
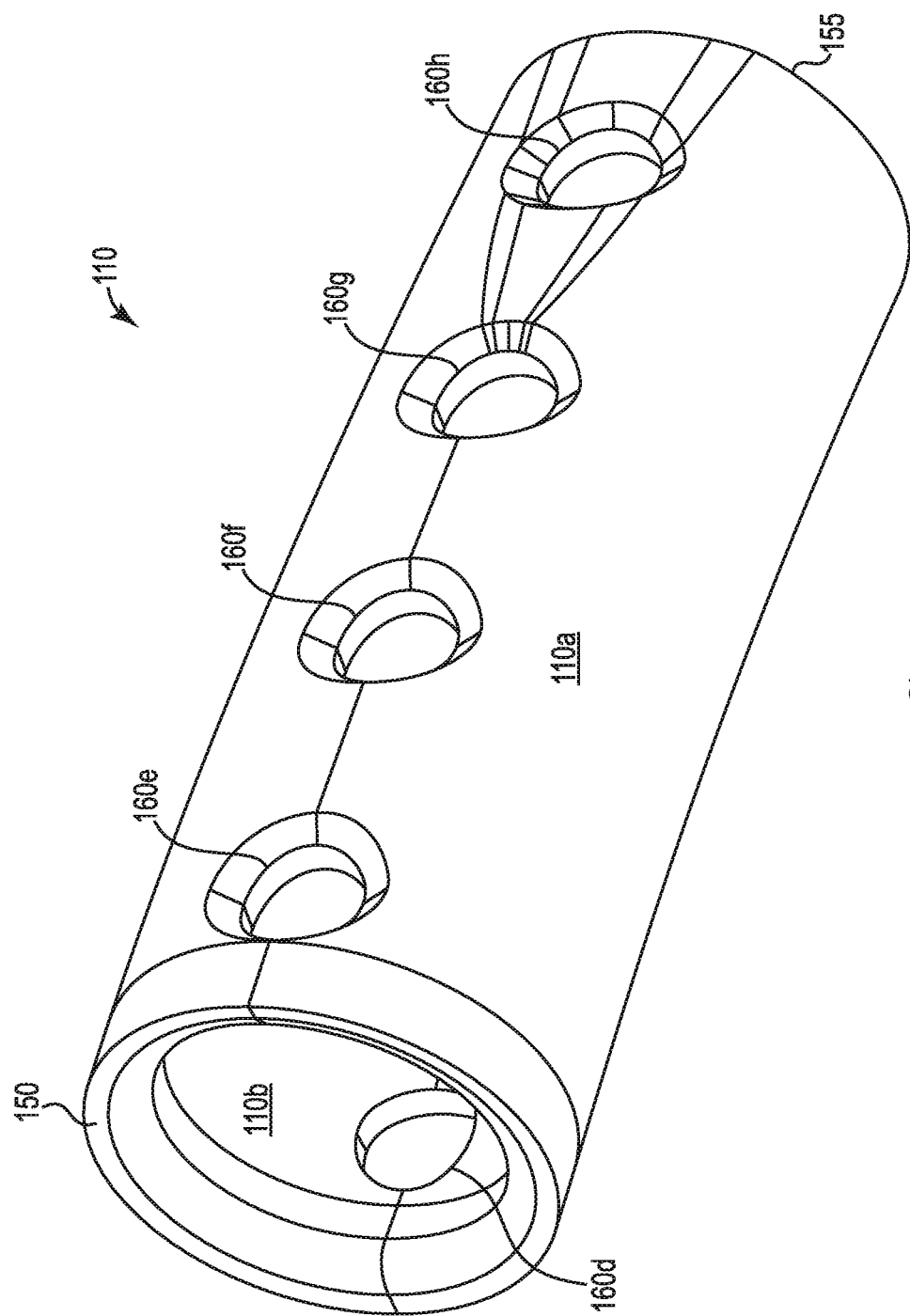
FIG. 6 is a perspective view of one embodiment of a support for the airway apparatus of FIG. 1.
Figure 7:
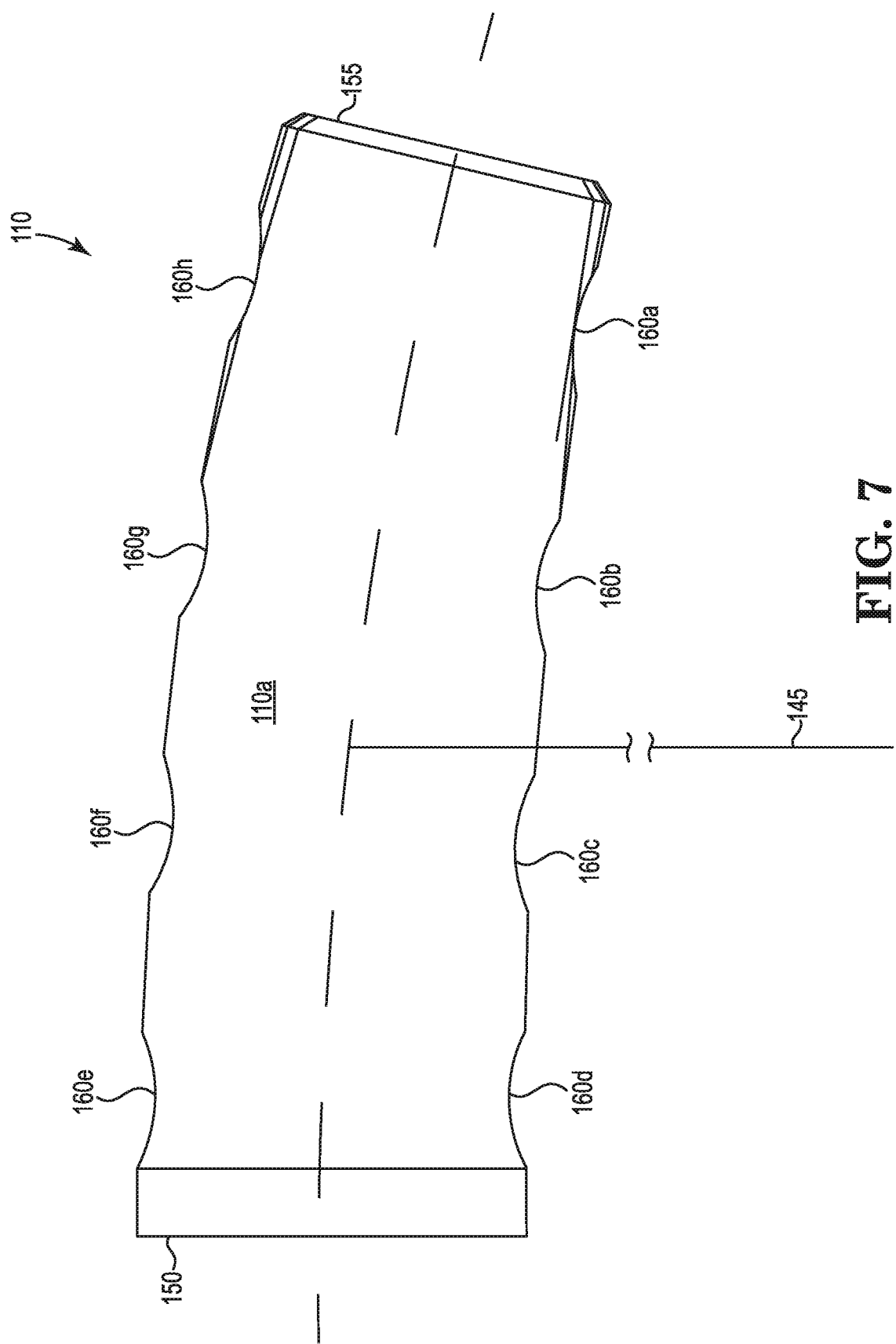
FIG. 7 is a side view of the support of FIG. 6.
Figure 8:
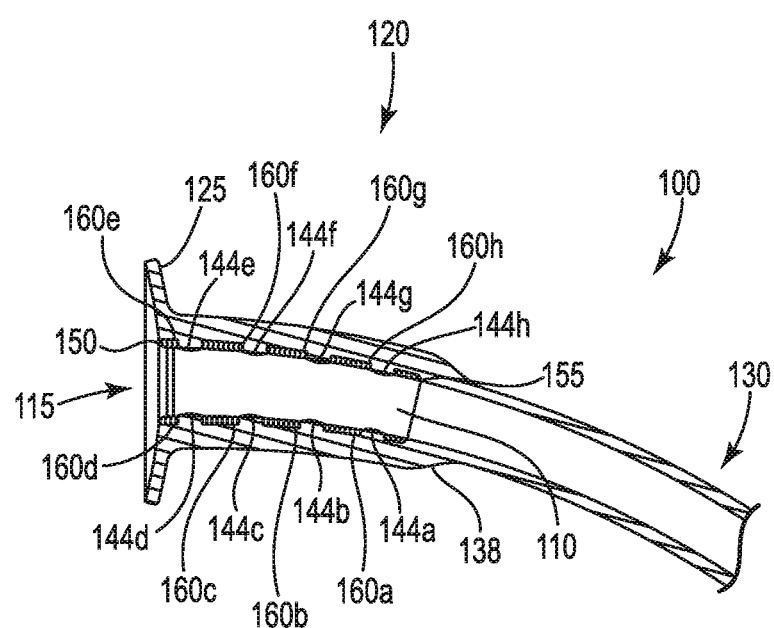
FIG. 8 is an enlarged partial view of a proximal portion of the airway apparatus of FIG. 1.
Figure 15A:
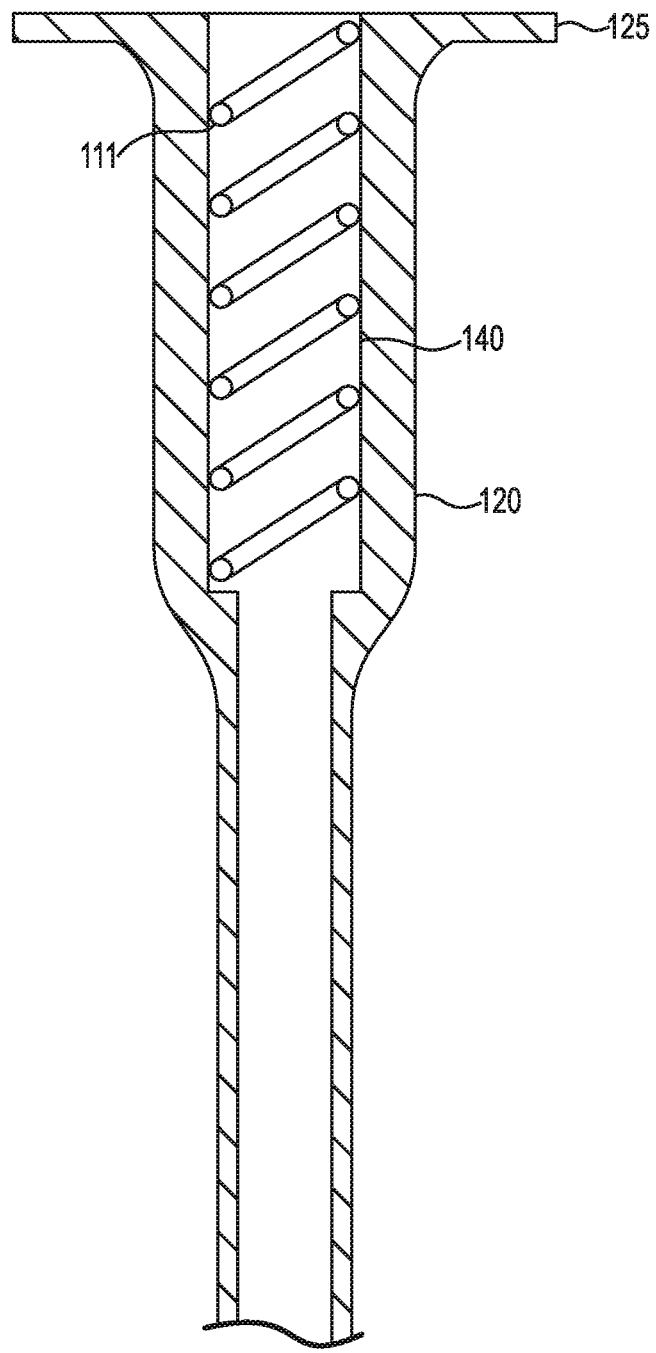
FIG. 15A is a diagrammatic longitudinal cross-sectional view of an alternative embodiment of a helical support structure for an airway apparatus.
Figure 15B:
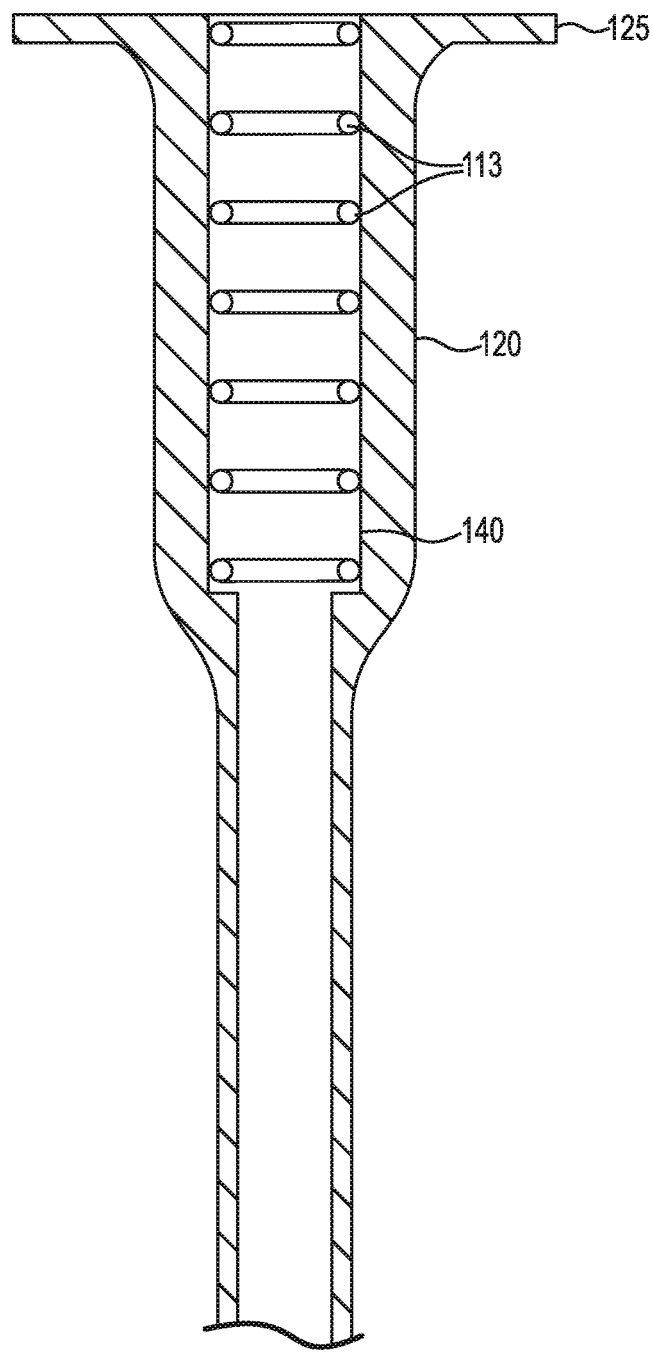
FIG. 15B is a diagrammatic longitudinal cross-sectional view of one alternative embodiment of an annular support structure for an airway apparatus.
Figure 15C:
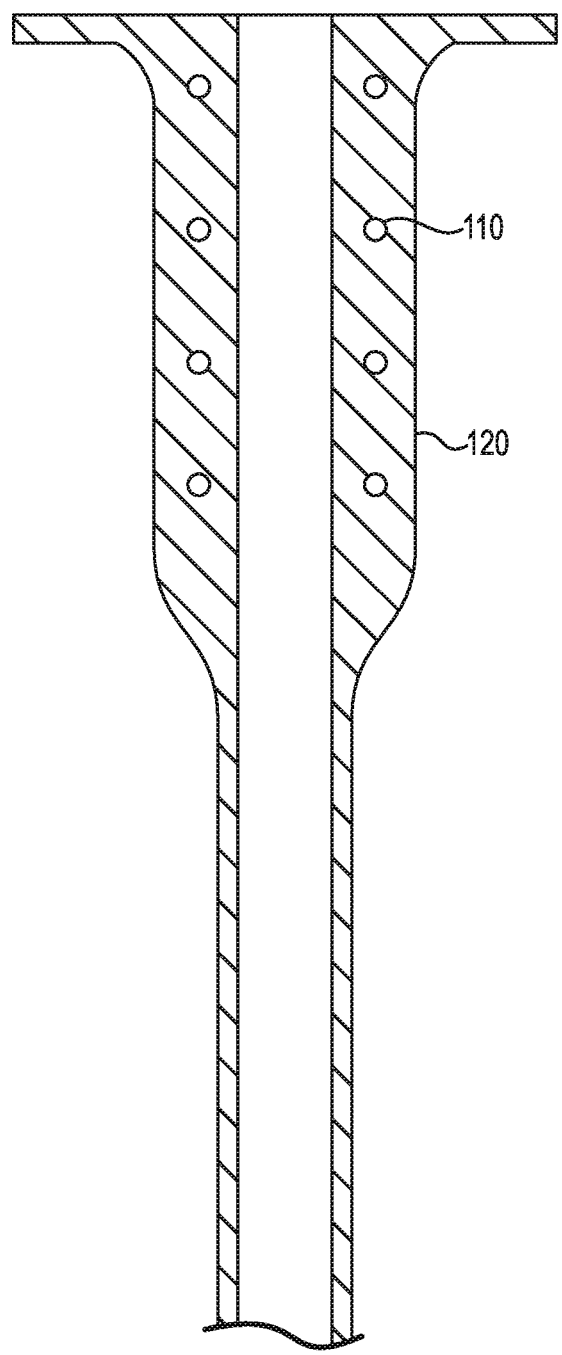
FIG. 15C is a diagrammatic longitudinal cross-sectional view of an additional alternative embodiment of a support structure for an airway apparatus.

With reference to FIGS. 6 and 7, in one embodiment, the illustrated support 110 is generally a tubular sleeve having an outer surface 110a and an inner surface 110b. Outer surface 110a has an outer diameter sized to fit within the inner diameter of cavity 140 of upper portion 120. Inner surface 110b has an inner diameter that is generally the same as the inner diameter of the lumen in the lower portion 130. In one embodiment, support 110 is made of a hard (e.g., non-compressible) medical grade polypropylene or polyethylene terephthalate in a molding process. In one embodiment, support 110 has a slightly curved axis 145; however, in other embodiments, the support 110 has a straight linear axis. In one embodiment, support 110 includes a tapering inner and outer diameter that reduces in dimension from a first end 150 to a second end 155 of support 110. As positioned within cavity 140, first end 150 of support 110 is located adjacent the flange 125 and the second end 155 is adjacent to the lower portion 130 in contact with radial shoulder 143. Radial shoulder prevents movement of support 110 in the distal direction. In other embodiments, the support 110 may include a uniform inner and/or outer diameter (See FIG. 10). In the illustrated embodiment, the insert 110 includes a plurality of apertures 160 (e.g., apertures 160a, 160b, 160c, 160d, 160e, 160f, 160g, 160h). In other embodiments, the insert 110 may include more or less than eight apertures 160. In further embodiments, the apertures 160 may be omitted. In yet alternative embodiments, Support 110 may comprise, for example, a structural framework that provides radial support to upper portion 120 of tube 105, such as a helical member 111 or a plurality of linearly spaced annular members 113, as shown in FIGS. 15a and 15b. Helical member 111 and annular members 113 may be made of a medical grade metal or polymer. As shown in FIG. 15c, in one embodiment, support 110 can be molded within the wall of upper portion 120.

Figure 10:
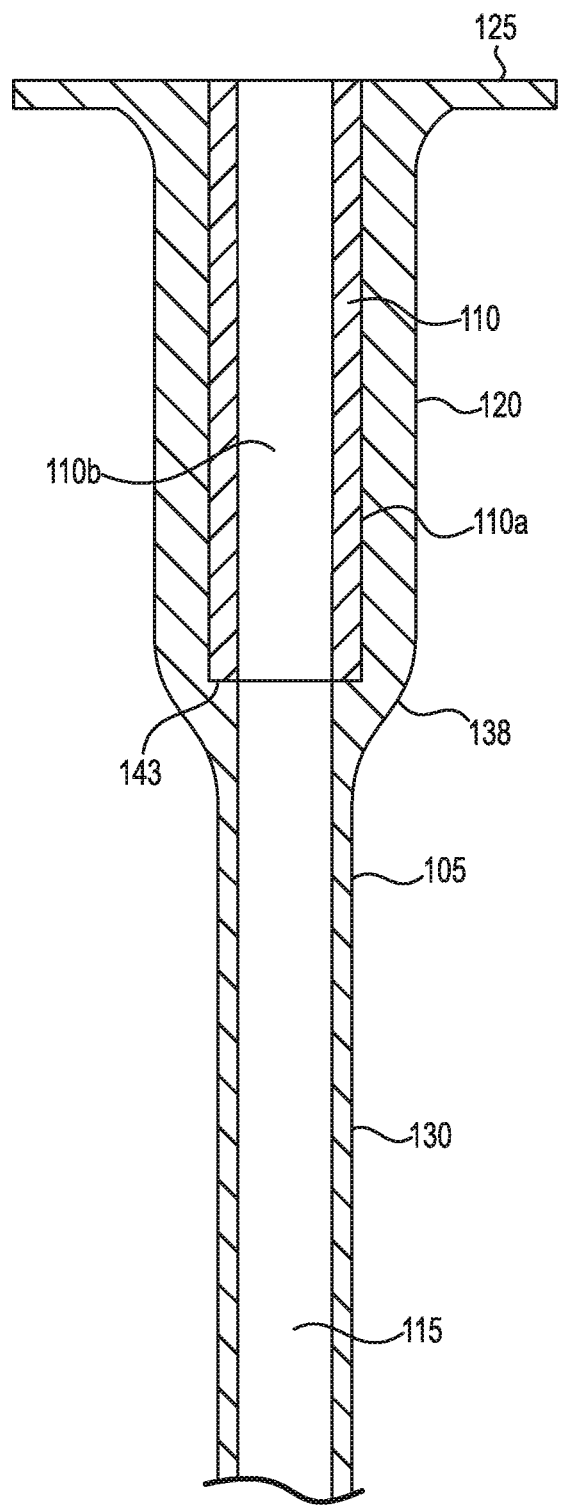
FIG. 10 is a diagrammatic longitudinal cross-sectional view of a proximal portion of an alternative embodiment of support structure for an airway apparatus.

In one embodiment, support 110 is secured from movement within the cavity 140 by each protrusion 144 engaging a corresponding aperture 160 (e.g., the first protrusion 144a engages the first aperture 160a). In an alternative embodiment, where the protrusions 144 and the apertures 160 are omitted, support 110 may be held within the cavity 140 by a frictional interference fit. As shown in FIG. 10, in an alternative embodiment, airway apparatus 100 may be made in a two-shot molding process, with support 110 molded in the first shot, and tube 105 molded over support 110 in a second shot, which secures support 110 within tube 105. In other embodiments, support 110 may be selectively removable from the cavity 140 by disengagement of the protrusions 144 and the corresponding apertures 160. In further embodiments, the outer surface of support 110 may be fixed to the inner surface of cavity 140 by a medical grade adhesive.

Figure 11A:
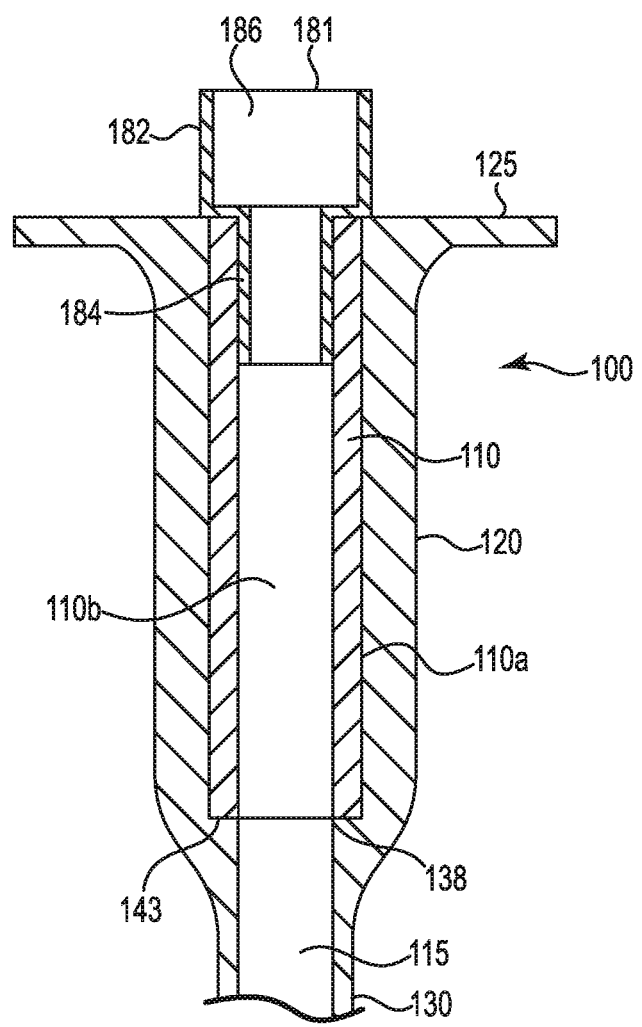
FIG. 11A is a diagrammatic longitudinal cross-sectional view of the airway apparatus of FIG. 10 in use with a coupler to connect the airway apparatus to a medical breathing device.
Figure 11B:
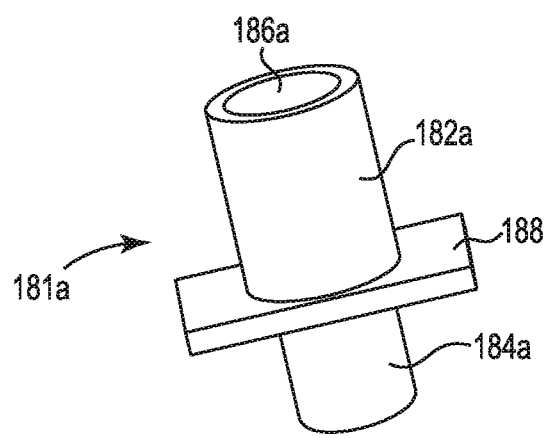
FIG. 11B is a side perspective view of an alternative coupler for use with the airway apparatus of FIG. 10.

The airway apparatus 100 is operable to be directly or indirectly coupled to a medical breathing device, for example, an anesthesia circuit, manual resuscitator/self-inflating bag, which will be referred to as a medical breathing device hereafter, or may not be coupled to another device. For example, as shown in FIG. 11A, a tubular connector 181 having a first tubular portion 182 and a second tubular portion 184 and a lumen 186 may be used to couple the airway apparatus 100 to such medical breathing devices. The outer surface diameter of first tubular portion 182 is sized to attach to a coupler of a medical breathing device, while the outer surface diameter of the second tubular portion 184 is sized to fit within and frictionally engage inner surface 110b of support 110. Alternatively, as shown in FIG. 11B, a tubular connector 181a having a first tubular portion 182a, a second tubular portion 184a, a lumen 186a, and a flange/separator 188 between the first tubular portion 182a and the second tubular portion 184a may be used to couple the airway apparatus 100 to such medical breathing devices. Here, the second tubular portion 184a of the connector 181a is insertable into support 110, and the first tubular portion 182a receives or is inserted into a connecting portion of a medical breathing device, such as previously described. The separator 188 serves to prevent airway apparatus 100 from entering the oral cavity of a patient. Separator 188 may have other shapes as previously discussed in reference to flange 125. A similar connector is disclosed, for example, in U.S. Pat. No. 8,631,795, which discloses an airway used in combination with a connector to be coupled to an anesthesia circuit, or a medical breathing device, the disclosure of which is incorporated herein by reference. Airway apparatus 100 used with a connector that incorporates a separator between the first and second tubular ends can thus be formed without flange 125, with the separator preventing the airway apparatus from entering the oral cavity of a patient. In some instances, the connector is integral with the medical breathing device and the airway apparatus 100 is, therefore, directly coupled to the medical breathing device via the integral connector. The connector can also be directly coupled to a medical breathing device, which delivers oxygen closer to the vocal cords. With reduce diffused oxygen around the surgical field the fire risk will be dramatically eradicated.

Figure 9:
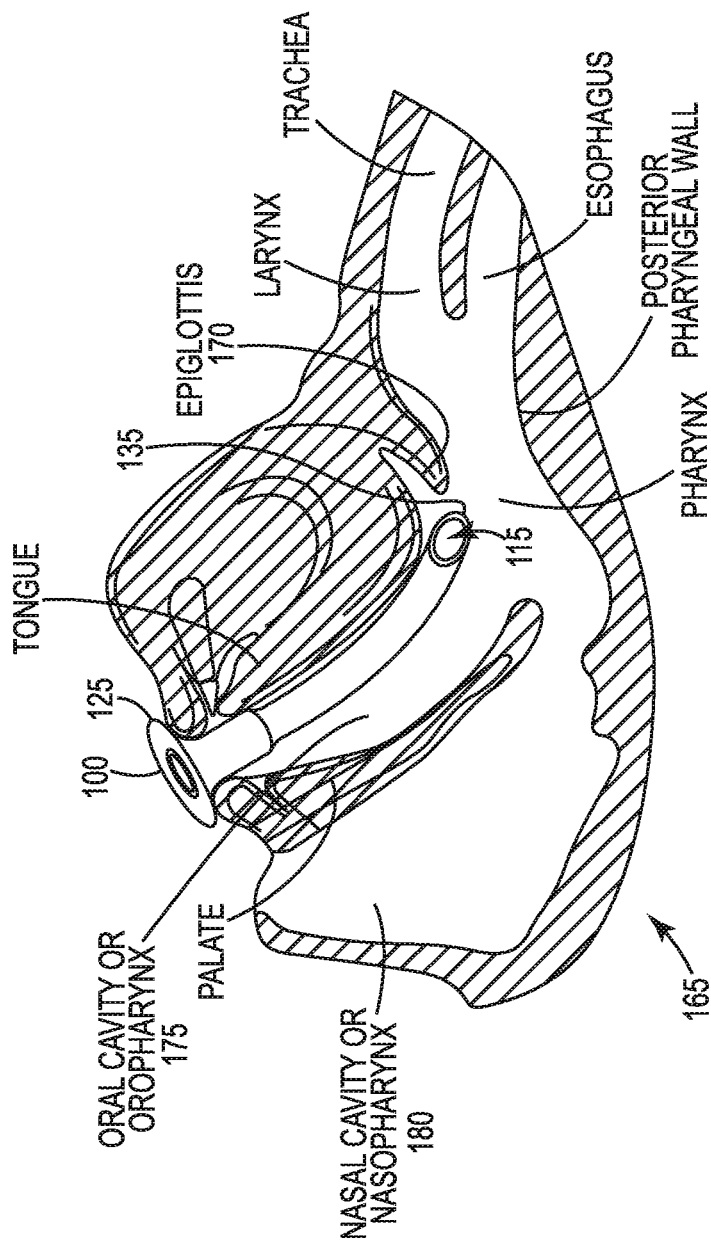
FIG. 9 illustrates the airway apparatus of FIG. 1 positioned in the oral cavity of a patient.
Figure 14A:
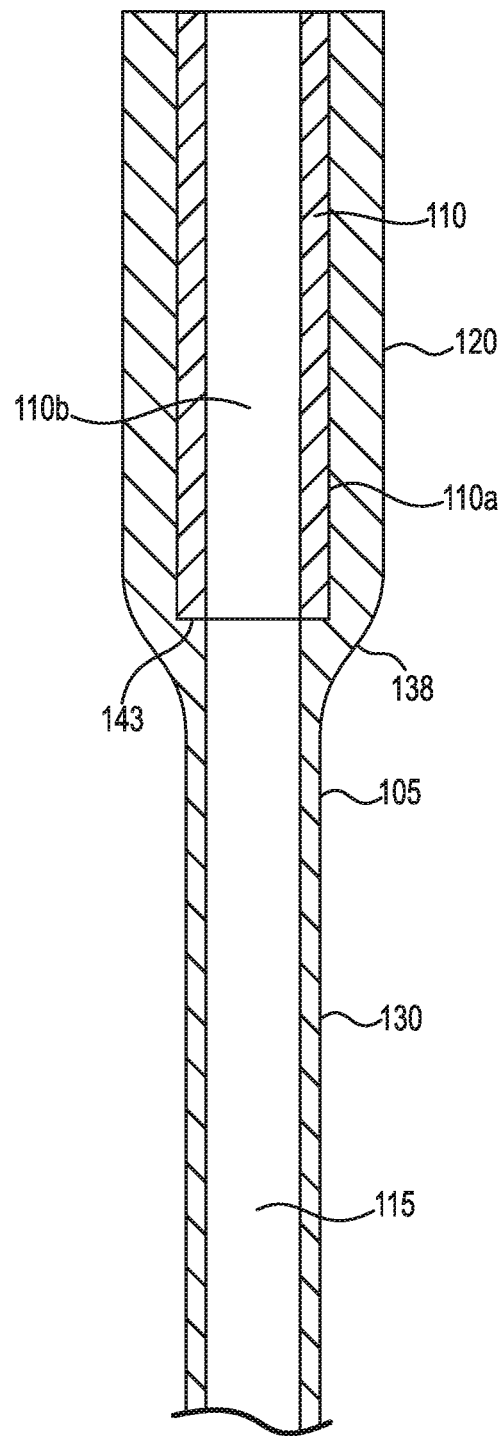
FIG. 14A is a diagrammatic longitudinal cross-sectional view of an alternative embodiment of an airway apparatus with a support structure.
Figure 14B:
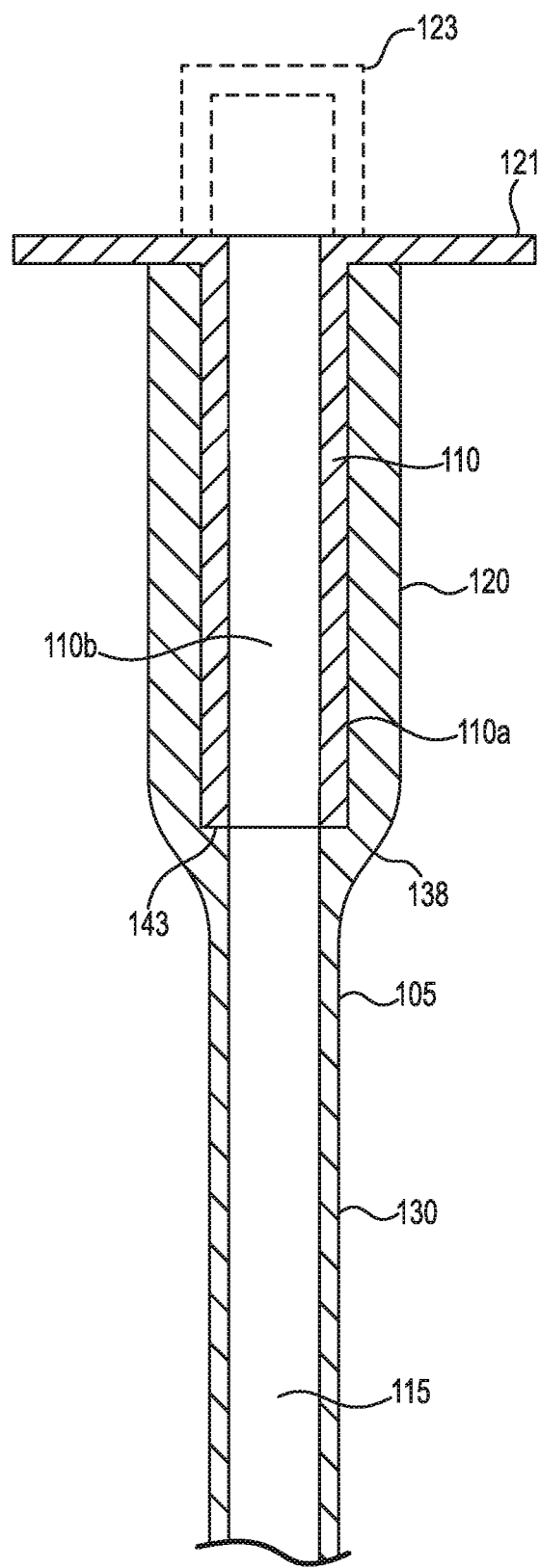
FIG. 14B is a diagrammatic longitudinal cross-sectional view of an alternative embodiment of an airway apparatus with alternative embodiments of a support structure that incorporates a flange and an optional coupler for connecting another medical device.

The airway apparatus 100 can be used without a tubular connector 181 with or without an oxygen source. With reference to FIG. 9, the bevel end 135 of the tube 105 is designed for comfort and gentle insertion into a patient's airway (e.g., the pharynx of a patient 165). In the illustrated embodiment, the bevel end 135 does not extend beyond the epiglottis 170 of the patient 165. When flange 125 contacts the exterior surface of the patient's face around the mouth, the flange 125 prevents the airway apparatus 100 from entering the oral cavity 175 of the patient 165, and locates the upper portion 120 such that the upper portion 120 generally extends to the molars of the patient 165. In an alternative embodiment, flange 125 can be omitted from the flexible tube 105, in which case flexible tube 105 is held in position by securing it to the patient with, for example tape (See, e.g., FIG. 14A). Alternatively, as shown in FIG. 14B, support 110 can incorporate a flange 121 that is external to the proximal end of tube 105, as well as an optional coupler 123 (shown in phantom) that can extend from flange 121 and allow for connection of another medical device, such as a medical breathing device.

The use of support 110 within the upper portion 120 of flexible tube 105 prevents the patient 165 from biting down and closing off the airway 115. Moreover, the flexible tube 105 surrounds support 110 so that the flexible tube 105 provides cushioning to prevent the patient 165 from harming their teeth in the event the patient bites on the airway apparatus 100. As illustrated, (e.g., in FIG. 1), the upper portion 120 includes a larger outer diameter than the lower portion 130. The larger diameter of the upper portion 120 is, at least in part, due to the increase in thickness of the wall of flexible tube 105 at the upper portion 120 relative to the lower portion 130. In one embodiment, the wall thickness of the upper portion 120 is about 4.0 to about 12.0 millimeters. In alternative embodiments, the wall thickness of the flexible tube 105 is uniform between the upper portion 120 and lower portion 130, and still provides cushioning for the rigid insert 110.

The airway apparatus 100 can be inserted into the airway cavity 180 of the patient 165 to create a patent airway. In some instances, airway apparatus 100 can be used to eliminate obstructions in the upper airway, such as caused by sleep apnea. Additionally, airway apparatus 100 can reduce or eliminate snoring when worn by a sleeping patient. The airway apparatus 100 also can be used to create airways in animals in veterinary applications.

Airway apparatus 100 can also be used with other medical devices. For example, an oxygen mask can be placed over the patient's nose and mouth or nasal cannula in the OMA to improve oxygenation and ventilation. Also, an OMA can be inserted alongside of the ETT or laryngeal mask airway (LMA) to prevent the patient from biting and collapsing the ETT or LMA. A medical breathing device can be coupled to the connecting portion to provide intraoral ventilation. An anesthesia breathing circuit can be coupled to the connecting portion to decrease the fire risk and improve ventilation.

Airway apparatus 100 eliminates upper airway obstruction in patients by keeping the airway patent. It consists of a flexible tube with a built in non-collapsible cushioned bite block that can be coupled with a rigid connector. Airway apparatus 100 eliminates many of the adverse effects associated with the currently used oropharyngeal airway (OA) and nasopharyngeal/nasal airway (NA). The airway apparatus lowers the risk of oral and nasal injury seen in OA and NA use. It also eliminates the concern of airway collapse due to biting, and prevents damage to other medical devices, such as when used alongside of an endotracheal tube (ETT), a laryngeal mask airway (LMAs), or other device. Airway apparatus 100 provides an alternative to a difficult mask ventilation by use with the rigid connector that may be directly coupled to an anesthesia breathing circuit or a medical breathing device. The connector can also be connected directly to an oxygen source, which decreases the fire risk associated with supplemental oxygen via open delivery systems. Finally, the decreased need for a jaw thrust/chin lift when applying the airway provides an easy hand off approach to airway management.

Thus, the airway apparatus disclosed provides, among other things, an enhanced airway to provide a safe, comfortable airway in a patient. Furthermore, the disclosed apparatus may be adapted for use in or in association with other medical devices that are inserted into the mouth of a patient, such as, e.g., endotracheal tubes, laryngeal mask airways, supraglottic airways, endoscopes, fiberoptics, esophageal catheters, and the like. Various aspects of the airway apparatus 100 are set forth in the following claims.

The invention claimed is:

1. An oral airway comprising:
a flexible tube having a proximal end, a distal end, a flange at the proximal end, an upper portion adjacent to the flange, a lower portion connected to the upper portion and extending to the distal end, and a lumen defined by an inner surface of the flexible tube that extends from the proximal end to the distal end, the upper portion positionable, in a patient's mouth with the flange external to the patient's mouth, the distal end able to extend no further than the patient's epiglottis, the upper portion and the lower portion each having a uniform inner diameter and outer diameter, the inner diameter and outer diameter of the upper portion being, greater than the inner diameter and outer diameter of the lower portion, wherein the inner surface of the flexible tube forms a radial shoulder at a transition between the upper portion and the lower portion, and at least a portion of the flange has an outer diameter that is greater than an outer diameter of the upper portion;
and a tubular support positioned within the upper portion, the tubular support having an outer diameter sized to fit in the lumen of the upper portion, the tubular support further having an end in contact with the radial shoulder, and an inner tubular surface to allow airflow from the proximal end to the distal end of the flexible tube.

2. The oral airway of claim 1, wherein the outer diameter of the upper portion is between 1.6 to 2.1 centimeters, and the outer diameter of the lower portion is between 6.7 to 10.7 millimeters.

3. The oral airway of claim 2, wherein the flexible tube has a tubular wall, the tubular wall of the upper portion having a wall thickness that is greater than that of the lower portion.

4. The oral airway of claim 3, wherein the wall thickness of the tubular wall of the upper portion is between about 4.0 to about 12.0 millimeters, and wherein the wall thickness of the tubular wall of the lower portion is about 3.5 millimeters.

5. The oral airway of claim 1, wherein the flexible tube is comprised of thermoplastic elastomer having a durometer of between about shore A 40-80, and wherein the tubular support is comprised of thermoplastic polyurethane.

6. The oral airway of claim 5, wherein the tubular support comprises a tubular sleeve.

7. The oral airway of claim 6 and further comprising a tubular connector having a first portion and a second portion and a lumen therethrough, the second portion having an outer diameter that is smaller than that of the first portion, the second portion being connectable within the tubular sleeve, the first portion being connectable to a medical breathing device.

8. The oral airway of claim 6, wherein the tubular sleeve comprises an outer surface, the outer surface of the tubular sleeve in contact with an inner surface of the flexible tube, the tubular sleeve having an inner surface, the inner surface defining an inner diameter of the tubular sleeve, the inner diameter being generally equal to an inner diameter of the lumen of the lower portion of the flexible tube.

9. The oral airway of claim 8, wherein the outer surface of the tubular sleeve comprises a protrusion.

10. The oral airway of claim 9, wherein the inner surface of the upper portion of the flexible tube is in engagement with the outer surface of the tubular sleeve.

11. The oral airway of claim 8, wherein the inner surface of the upper portion of the flexible tube includes one or more protrusions, and wherein the outer surface of the tubular sleeve defines one or more openings, the one or more protrusions being positioned within the one or more openings.

12. An oral airway comprising:
a flexible tube having a proximal end, a distal end, a lumen that extends from the proximal end to the distal end, an upper portion adjacent to the proximal end, a lower portion between the upper portion and the distal end, the upper portion positionable in a patient's mouth, wherein the flexible tube is configured to define a flange immediately adjacent to the upper portion so as to be external to the patient's mouth and so as to limit the distal end from extending beyond the patient's epiglottis, the upper portion having a first length and the lumen of the upper portion having a first inner diameter along the first length, the lower portion having a second length that is greater than the first length and the lumen of the lower portion having a second inner diameter along the second length, the second inner diameter being less than the first inner diameter so as to define a radial shoulder at the intersection of the upper portion and the lower portion; and
a tubular support having a third length approximating the first length, the tubular support positioned within and along the lumen of the first length of the upper portion of the flexible tube, the tubular support having an end in contact with the radial shoulder to prevent movement of the support in a distal direction, the tubular support having an inner diameter that is generally the same as the second inner diameter of the lumen of the lower portion, the tubular support providing radial support of the upper portion to prevent blockage of the lumen.

13. The oral airway of claim 12 and further comprising a tubular connector, a first portion of the tubular connector being positioned within the tubular support, a second portion of the tubular connector being external to the proximal end of the flexible tube.

14. The oral airway of claim 12, wherein the upper portion has an outer diameter that is greater than that of the lower portion.

15. The oral airway of claim 14, wherein the flexible tube has a tubular wall, the tubular wall of the upper portion having a wall thickness that is greater than that of the lower portion.

16. The oral airway of claim 15, wherein the wall thickness of the tubular wall of the upper portion is between about 4.0 millimeters to about 12.0 millimeters.

17. The oral airway of claim 12, wherein the flexible tube is comprised of thermoplastic elastomer, and wherein the tubular support is comprised of thermoplastic polyurethane.

18. The oral airway of claim 17, wherein the tubular support comprises a tubular sleeve.

19. The oral airway of claim 18, wherein the tubular sleeve comprises an outer surface, the outer surface of the tubular sleeve in contact with an inner surface of the flexible tube.

20. The oral airway of claim 19, wherein the outer surface of the tubular sleeve comprises a protrusion.

21. The oral airway of claim 20, wherein the flexible tube comprises an inner surface, the inner surface of the upper portion of the flexible tube is in engagement with the outer surface of the tubular sleeve.

22. The oral airway of claim 19, wherein the flexible tube comprises an inner surface, the inner surface of the upper portion of the flexible tube includes one or more protrusions, and wherein the outer surface of the tubular sleeve defines one or more openings, the one or more protrusions being positioned within the one or more openings.

23. An oral airway comprising:
a soft, flexible tube having a proximal end and a distal end, the tube configured to define a flange at the proximal end, the tube further having an upper portion adjacent to the flange, the tube further having a lower portion between the upper portion and the distal end, and a lumen that extends from the proximal end to the distal end, wherein at least a portion of the flange has an outer diameter that is greater than an outer diameter of the upper portion;
a tubular sleeve positioned within the upper portion of the tube that provides radial support of the upper portion and allows airflow from the proximal end to the distal end of the tube; and
a tubular connector having a first portion and a second portion and a lumen therethrough, the second portion having an outer diameter that is smaller than that of the first portion, the second portion being connectable within the tubular sleeve, the first portion being connectable to a medical breathing device.

* * * * *